United States Patent [19]

Robinson

[11] Patent Number: 4,503,206

[45] Date of Patent: Mar. 5, 1985

[54] α,ω-PERFLUORODICARBOXYLIC ACIDS

[75] Inventor: Ivan M. Robinson, Wilmington, Del.

[73] Assignee: Indiana University Foundation, Bloomington, Ind.

[21] Appl. No.: 452,393

[22] Filed: Dec. 22, 1982

[51] Int. Cl.$^3$ ............................................... C07C 55/02
[52] U.S. Cl. ................... 526/255; 525/326.2; 525/539; 528/381; 528/388; 528/401; 562/596; 562/524
[58] Field of Search .................. 526/93, 250, 229, 234, 526/255; 562/596; 528/381, 388

[56] References Cited

U.S. PATENT DOCUMENTS 3,714,137  1/1973  Tienhard ............................ 526/255

FOREIGN PATENT DOCUMENTS 645703   7/1962  Canada ............................... 562/596
758419  10/1956  United Kingdom ................ 526/255

OTHER PUBLICATIONS

Berry et al., Nov. 1951, J. A. Chem. Soc., vol. 73, pp. 5195–5197.

Primary Examiner—Joseph L. Schofer
Assistant Examiner—Peter F. Kulkosky
Attorney, Agent, or Firm—Kirkland & Ellis

[57] ABSTRACT

Tetrafluoroethylene is reacted in an aqueous environment with hydroxyl radicals, generating a mixture of water soluble and water insoluble α,ω-perfluorodicarboxylic acids.

9 Claims, No Drawings

α,ω-PERFLUORODICARBOXYLIC ACIDS

BACKGROUND OF THE INVENTION

1. Field of the Invention

This invention relates to a controlled free radical oligomerization of tetrafluoroethylene and a means of introducing carboxylic acid functionality at the ends of each chain.

2. Description of the Prior Art

Synthetic routes to perfluorodicarboxylic acids have commonly involved the oxidative cleavage of carbon-carbon double bonds such as those present in perfluorocycloalkenes or perfluorodiolefins. The free radical polymerization of tetrafluoroethylene to give high molecular weight insoluble and somewhat intractable polymer is known. The use of aqueous peroxydisulfate as an initiator has been shown to produce high molecular weight insoluble polymers is also known. However, the established use of free radical initiator concentrations for tetrafluoroethylene is substantially below 0.5% by weight of the reaction medium, and preferably below 0.1% by weight.

The paper by K. L. Berry and J. H. Peterson, J. Am. Chem. Soc., 73, 5195 (1951) describes the free radical polymerization of tetrafluoroethylene using aqueous peroxydisulfate in concentrations of about 0.05% by weight, and ferrous iron concentrations of about 2 parts per million. However, this polymerization of tetrafluoroethylene produced a high molecular weight insoluble and somewhat intractable polymer with number average molecular weight of about 142,000 to about 534,000.

The paper by M. I. Bro and C. A. Sperati, J. Polymer Sci., 38, 289 (1959), also describes the use of aqueous peroxydisulfate initiator for the polymerization of tetrafluoroethylene which produced only high molecular weight polymer (350,000 to 2,150,000 g/m). Concentrations of the peroxydisulfate were low, and ranged from about 0.2 to about 0.4% by weight. Furthermore, only a small amount of the peroxydisulfate was consumed because the polymerization was performed in the absence of a promoter.

Syntheses of α,ω-perfluorodicarboxylic acids are known. The *Kirk-Othmer Encyclopedia of Chemical Technology*, (2nd Ed., Wiley: New York, 1970) Vol. 9, pg. 774, describes the individual syntheses of $HOOC(CF_2)_nCOOH$ wherein n=1, 2, 3, 4. The paper by R. A. Mitsch, P. H. Ogden, and A. H. Stoskopf, J. Org. Chem., 35, 2816 (1970) describes the synthesis of α,ω-perfluorodicarboxylic acids wherein n=6, 9, and 12. Other papers describe the synthesis of α, ω-perfluorodicarboxylic acids wherein n=4, 6, 8, 12 (I. L. Knunyants, Chih-Yuan Li, and V. V. Shokina (Chem. Abs. 56, 302 (1962)); and wherein n=3, 4 (E. T. McBee, P. A. Wiseman, and D. D. Bachmann, Ind. Eng. Chem., 39, 415 (1947)). However, none of the above references describe the use of relatively high, above 0.5% by weight, free radical initiator concentrations for the synthesis of α,ω-perfluorodicarboxylic acids and the mixtures formed thereby, by the methods of the present invention.

It is therefore an object of the present invention to provide a synthesis of α,ω-perfluorodicarboxylic acids via a controlled free radical oligomerization reaction.

It is a further object of this invention to produce mixtures of said α,ω-perfluorodicarboxylic acids of both even- and odd-numbered chain lengths.

It is a further object of this invention to use high concentrations of free radical initiators in order to control oligomerization.

SUMMARY OF THE INVENTION

The foregoing and other objects, advantages and features of this invention may be achieved by reacting tetrafluoroethylene with a source of hydroxyl radicals in an aqueous environment, thereby producing oligomeric α,ω-perfluorodicarboxylic acids of even- and odd-numbered chain lengths of the general formula $HOOC(CF_2)_nCOOH$, wherein n=1 to about 1000. The source of hydroxyl radicals is most conveniently a peroxydisulfate salt, and a metal ion promoter is used to assist the decomposition of the peroxydisulfate salt. The reaction is preferably carried out in the range of about 35° C. to about 100° C. with an initial concentration of the peroxydisulfate greater than about 0.5%. Performed in this manner, this method provides a facile route to perfluorocarbon chains with α,ω-carboxylic acid functionality. These products are strongly acidic and are of useful starting materials for producing polymers such as polyurethanes, polyamides and polybenzamidazoles.

DETAILED DESCRIPTION OF THE INVENTION

Tetrafluoroethylene is treated in an aqueous environment with a source of hydroxyl radicals in sufficient amount to control oligomerization. While hydrogen peroxide can be used as the source of hydroxyl radicals, it is preferred to use peroxydisulfate salts because the rate of decomposition to hydroxyl radicals can be readily controlled using promoters at specific temperature ranges. Sodium, potassium, and ammonium peroxydisulfates are preferred because of their relatively high solubility in water.

It is desirable to use a metal ion promoter to activate and control the decomposition of the peroxydisulfate salt at temperatures in the range from about 0° C. to about 110° C. Thermal decomposition of peroxydisulfate proceeds slowly, if at all, in this temperature range in the absence of a promoter. Typical promoters are ions of polyvalent metals which readily undergo oxidation-reduction reactions wherein the metal is selected from the group comprising iron, nickel, cobalt and copper.

The combination of peroxydisulfate with promoter in an aqueous media allows the use of relatively low reaction temperatures, namely from about 35° to about 100° C., in order to control the rate of hydroxyl radical formation. If the temperature is below about 35° C., radical formation will be slow, and limited amounts of lower oligomeric products will be formed.

The reaction of tetrafluoroethylene in an aqueous medium with a controlled source of hydroxyl radicals is conveniently carried out in pressure vessels such as stirred autoclaves operated in batchwise or continuous modes. The concentration of tetrafluoroethylene can be controlled by pressure and/or by dilution with an inert gas such as nitrogen or argon.

The products of this invention are perfluorocarbon chains with terminal carboxylic acid groups,

$HOOC(CF_2)_nCOOH$ wherein n=1 to about 1000.

Oligomers formed by the method of the present invention, wherein n=1 to about 9, are water soluble and were found to be crystalline solids melting over a range from about 35° to about 70° C. As used herein, the term "water soluble" conveniently denomiates those oligomers wherein n=1 to about 9. Of course, as one skilled in the art would appreciate, the n=10 oligomer as well as those oligomers wherein n is greater than 10 are partially soluble in water. Infrared spectra of cold-pressed thin films of the perfluorodicarboxylic acid oligomers show intense absorption bands for carboxylic acid functionality [3500-2500 cm$^{-1}$(OH) and 1750 cm$^{-1}$(C=O)], as well as characteristic bands for perfluoroalkyl groups. The mixture of perfluorodicarboxylic acids from a representative reaction was found to have a neutralization equivalent of about 170 g/eq, hence, a molecular weight of about 340 g/m. The products of the methods of the present invention are not monofunctional as evidenced by the fact that all known monofunctional perfluorocarboxylic acids possessing molecular weights less than 364 g/m are liquids at 20° C.

A portion of the water soluble perfluorodicarboxylic acid mixture was converted to the corresponding anhydride mixture, the anhydride mixture was then hydrolysed to the corresponding acid mixture and the acid mixture was converted to a mixture of methyl diesters. Methyl esters derived from the anhydride mixture were examined by mass spectroscopy and gas chromatography and components of the mixture proved to be identical to known samples, thus confirming the structures of the perfluorodicarboxylic acids. The water soluble perfluorodicarboxylic acid mixture was further characterized by gas chromatography and mass spectroscopy of the methyl diesters. Fractions wherein n=2 and 3 were compared with methyl diesters of authentic perfluorosuccinic and perfluoroglutaric acids and were found to be identical.

The portion of the reaction product which did not dissolve in water (hereinafter referred to as "water insoluble polymer"), was found to contain perfluorodicarboxylic acids wherein n is 10 or greater. Again, as one skilled in the art will appreciate, the "water insoluble oligomer" also contained small amounts of what was previously denominated "water soluble", namely perfluorodicarboxylic acids wherein n is less than 10. The infrared spectrum of a cold-pressed thin film of the water insoluble oligomer showed intense absorption bands, for carboxylic acid functionality [3500-2500 cm$^{-1}$(OH) and 1700 cm$^{-1}$(C=O)]. In a mixture of oligomeric diacids prepared from runs having high concentrations of iron or copper promoters the infrared spectrum shows some carboxylate anion [1675 cm$^{-1}$ C=O)] and the polymer possesses a red or blue discoloration.

Treatment of the water insoluble oligomeric mixture of perfluorodicarboxylic acids with diazomethane in ether permits the isolation of the product as a mixture of methyl diesters. The methyl diesters were analyzed by gas chromatography and mass spectroscopy techniques.

Mass spectral studies of methyl diesters from both water soluble and water insoluble oligomers gave ions in accordance with the homologous series structures. Unzipping of these ions by mass units of 100 ($C_2F_4$) and 50 ($CF_2$) was frequently observed.

Stepwise oligomerizaton of tetrafluoroethylene would normally be expected to generate only even-numbered carbon chains, and this is indeed the major reaction pathway because the dominant species found in the product, is HOOC($CF_2$)$_n$COOH, wherein n is an even number. However, odd-numbered oligomers are produced via a secondary reaction, namely, oxidative decarboxylation. The oxidative decarboxylation was demonstrated using perfluoroglutaric acid as a representative compound. Treatment of pure perfluoroglutaric acid with aqueous peroxydisulfate in the presence of ferrous ion formed predominantly perfluorosuccinic acid. A second oxidative decarboxylation forms some perfluoromalonic acid. The methods of the present invention and the compositions formed thereby are demonstrated by the following examples.

EXAMPLE I

The compositions of the present invention may be prepared by the following method. A solution of potassium peroxydisulfate (5.4 g) in 100 ml of distilled water was placed in an autoclave, with a total capacity of about 300 ml. Ferrous sulfate (200 mg) was placed in the autoclave, having been previously sealed in a fragile glass ampule which would rupture when the solution was stirred. The autoclave was then chilled in dry ice and alternately evacuated and repressurized with argon in order to deaereate the system. After heating the solution in the autoclave to about 65° C., the argon pressure was adjusted to about 10 psig, a stirrer was activated, and the ampule was broken. Tetrafluoroethylene was introduced to bring the total pressure of the system to about 40 psig. During a period of about 120 minutes, the tetrafluoroethylene pressure was repeatedly adjusted to maintain the total pressure of the system between about 38 and about 40 psig. Upon completion of the reaction, the autoclave was vented, and its contents were filtered through a sintered glass funnel. The autoclave was rinsed and the washings were filtered in order to recover the mixture of water insoluble perfluorodicarboxylic acid oligomers (about 1.1 g). The combined filtrates were treated with potassium iodide to destroy the unreacted peroxydisulfate. The combined filtrates were then distilled to remove iodine. After distillation the concentrate was extracted with ether, and the ether was removed. Solid crystalline oligomeric perfluorodicarboxylic acids (1.2 g) were obtained which melted in the range from about 35° C. to about 48° C.

The results for this Example are tabulated below in Table I, entry 3. The results for other experiments which illustrate typical reactions of tetrafluoroethylene with aqueous peroxydisulfate are also tabulated below. In all tabulated cases, unless indicated otherwise, the oligomerization was performed with an argon diluent (10 psig) and 100 ml of water, containing $K_2S_2O_8$ (5.4 g).

TABLE I

| Entry | $CF_2=CF_2$ (psig) | Additive | Temp. (°C.) | Time (min) | Product Weight (g) WS$^a$ | WI$^b$ | Peroxydisulfate Consumed (%)$^c$ |
| --- | --- | --- | --- | --- | --- | --- | --- |
| 1 | 40-50 | FeSO$_4$$^d$ | 20-25 | 100 | | 7.0 | |
| 2 | 28-30 | FeSO$_4$$^e$ | 60-70 | 180 | 0.4 | 0.9 | 27 |
| 3 | 38-40 | FeSO$_4$$^e$ | 65-75 | 120 | 1.2 | 1.1 | 71 |

TABLE I-continued

| Entry | CF$_2$=CF$_2$ (psig) | Additive | Temp. (°C.) | Time (min) | Product Weight (g) WS[a] | WI[b] | Peroxydisulfate Consumed (%)[c] |
|---|---|---|---|---|---|---|---|
| 4 | 44–51 | CuSO$_4$[f] | 80–90 | 80 | 1.9 | 1.6 | 72 |

[a]Water Soluble oligomer.
[b]Water Insoluble oligomer.
[c]Based on iodimetry.
[d]No Ar diluent, 2.7 g K$_2$S$_2$O$_8$, and 57 mg FeSO$_4$—7H$_2$O.
[e]0.20 g FeSO$_4$—7H$_2$O.
[f]40 mg CuSO$_4$ and 0.47 g copper powder with 8.1 g K$_2$S$_2$O$_8$.

The water soluble fraction of the reaction product mixture was converted with a solution of diazomethane in ether to a mixture of methyl diesters, analyzed by gas chromatography, and the relative area percent compositions of the components are tabulated below in Table II.

TABLE II

| H$_3$CO$_2$C(CF$_2$)$_n$CO$_2$CH$_3$ Composition | Area % |
|---|---|
| n = 1 | 1.6 |
| n = 2 | 30.3 |
| n = 3 | 5.1 |
| n = 4 | 28.4 |
| n = 5 | 2.2 |
| n = 6 | 13.3 |
| n = 7 | 1.3 |
| n = 8 | 12.2 |
| n = 9 | 0.6 |
| n = 10 | 3.8 |
| n = 11 | 0.3 |
| n above 11 | .9 |

EXAMPLE II

Potassium peroxydisulfate (8.1 g), 100 ml of water, and a promoter of 40 mg of copper powder sealed in a fragile glass ampule were placed in an autoclave. The autoclave was heated to between about 80° C. and about 90° C., and the autoclave was deaerated as described in Example I. The solution was stirred and the system was pressurized with argon (10 psig) and tetrafluoroethylene (44–51 psig) for about 2 hours. Water insoluble (1.9 g) and water soluble (1.6 g) oligomeric perfluorodicarboxylic acids were obtained after the reaction was worked-up in the manner described in Example I. A cold-pressed film of the oligomeric mixture had a blue discoloration even after the mixture had been extensively washed with water. The results for Example II are tabulated in Table I, entry 4.

EXAMPLE III

The oxidative decarboxylation of perfluoroglutaric acids is demonstrated as follows. Perfluoroglutaric acid (1.2 g) was dissolved in 25 ml of deionized water containing K$_2$S$_2$O$_8$ (1.35 g). The solution was heated to about 80° C., stirred, and FeSO$_4$-7H$_2$O (28 mg) added. Iodometric titrations of aliquots taken after 1 and 2 hours showed that 64% and 81%, respectively, of the peroxydisulfate reacted. After 2 hours, a 2 g sample of the solution was treated with an ethereal solution of diazomethane. Gas chromatographic analysis of the methyl diesters indicated that about 32% of the perfluoroglutaric acid was converted to a mixture of perfluorosuccinic acid (57%), and perfluoromalonic acid (14%).

I claim:

1. A method for producing oligomeric α,ω-perfluorodicarboxylic acids of even- and odd-numbered chain lengths, of the general formula HOOC(CF$_2$)$_n$COOH, wherein n=1 to about 1000, comprising the step of:
  reacting tetrafluorethylene with an inorganic source of hydroxyl radicals in an aqueous environment.

2. The method of claim 1 in which the source of hydroxyl radicals is a peroxydisulfate salt.

3. The method of claim 2 in which a metal ion promoter is used to assist peroxydisulfate decomposition.

4. The method of claim 3 carried out in the temperature range of about 35° to about 100° C.

5. The method of claim 2 in which the initial concentration of peroxydisulfate in water is greater than about 0.5% by weight.

6. Perfluorodicarboxylic acid oligomers formed by the method of claim 1.

7. A composition comprising a water soluble homologous series of perfluorodicarboxylic acids of the general formula HOOC(CF$_2$)$_n$COOH, wherein n=1–9.

8. The composition of claim 7 wherein the composition possesses a neutralization equivalent of about 95 to about 200.

9. A composition comprising a water insoluble homologous series of perfluorodicarboxylic acid oligomers of the general formula HOOC(CF$_2$)$_n$COOH, wherein n=10 to about 1000.

* * * * *